United States Patent
Clair

(10) Patent No.: US 9,113,922 B2
(45) Date of Patent: Aug. 25, 2015

(54) CUSTOMIZED DRILLING JIG FOR IMPLANTATION OF A HEARING AID

(75) Inventor: Pierre-Yves Clair, Ambilly (FR)

(73) Assignee: Phonak AG, Stäfa (CH)

( * ) Notice: Subject to any disclaimer, the term of this patent is extended or adjusted under 35 U.S.C. 154(b) by 130 days.

(21) Appl. No.: 13/580,696

(22) PCT Filed: Feb. 23, 2010

(86) PCT No.: PCT/EP2010/052240
§ 371 (c)(1),
(2), (4) Date: Oct. 25, 2012

(87) PCT Pub. No.: WO2010/061006
PCT Pub. Date: Jun. 3, 2010

(65) Prior Publication Data
US 2013/0041381 A1 Feb. 14, 2013

(51) Int. Cl.
*A61B 17/17* (2006.01)
*A61B 19/00* (2006.01)

(52) U.S. Cl.
CPC ........... *A61B 17/1739* (2013.01); *A61B 17/171* (2013.01); *A61B 17/17* (2013.01); *A61B 19/20* (2013.01); *A61B 2019/5483* (2013.01)

(58) Field of Classification Search
CPC .. A61B 17/17; A61B 17/1703; A61B 17/171; A61B 17/1739; A61B 17/176; A61B 2017/1771; A61B 2017/1785; A61B 2019/204; A61B 19/20; A61C 1/082
USPC ........... 606/86 R, 96–98, 53, 80, 87; 433/72, 433/75, 76
See application file for complete search history.

(56) References Cited

U.S. PATENT DOCUMENTS

| 6,096,048 A | 8/2000 | Howard, III et al. |
| 2004/0015176 A1 | 1/2004 | Cosman |
| 2006/0247517 A1* | 11/2006 | Labadie et al. ................ 600/426 |
| 2011/0171593 A1* | 7/2011 | Ross ............................... 433/41 |

FOREIGN PATENT DOCUMENTS

| DE | 197 28 864 A1 | 1/1999 |
| DE | 100 49 938 A1 | 5/2002 |
| GB | 2 213 066 A | 8/1989 |
| WO | WO 2008117323 A1 * | 10/2008 |

* cited by examiner

*Primary Examiner* — Michael T Schaper
*Assistant Examiner* — Tracy Kamikawa
(74) *Attorney, Agent, or Firm* — Roberts Mlotkowski Safran & Cole, P.C.; David S. Safran

(57) ABSTRACT

A method of producing a drilling jig for implantation of a hearing aid involves capturing a molded imprint (14) of a patient's upper teeth (12) by solidifying an elastic material on them; connecting the teeth print to a jig (16) having a lateral beam (20) and navigation benchmarks (22); positioning the jig on the patient's head (10) using the imprint; capturing a three-dimensional image of the patient's head with the jig in place; determining a minimal invasive drilling axis (28) for hearing aid implantation based on the three-dimensional image; and manufacturing a customized jig having a drilling guide opening (24) in the lateral beam of the jig for guiding a drilling tool (26). The position and orientation of the drilling guide opening are selected to guide the drilling tool along the determined minimal invasive drilling axis when the jig is positioned on the patient's head by using the imprint (14).

10 Claims, 2 Drawing Sheets

FIG. 5
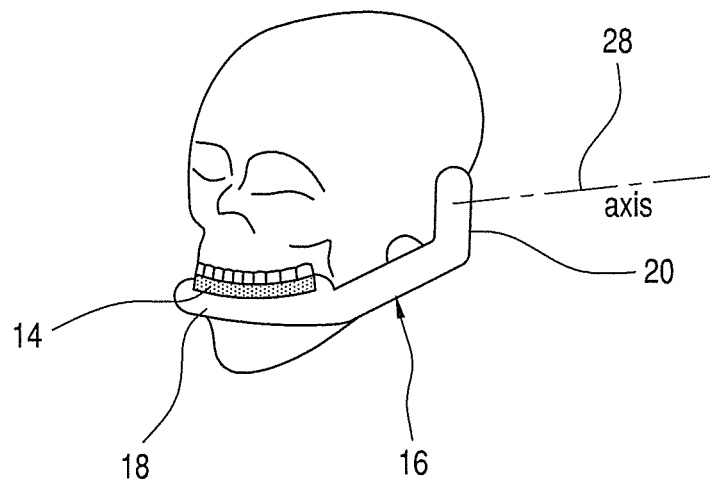
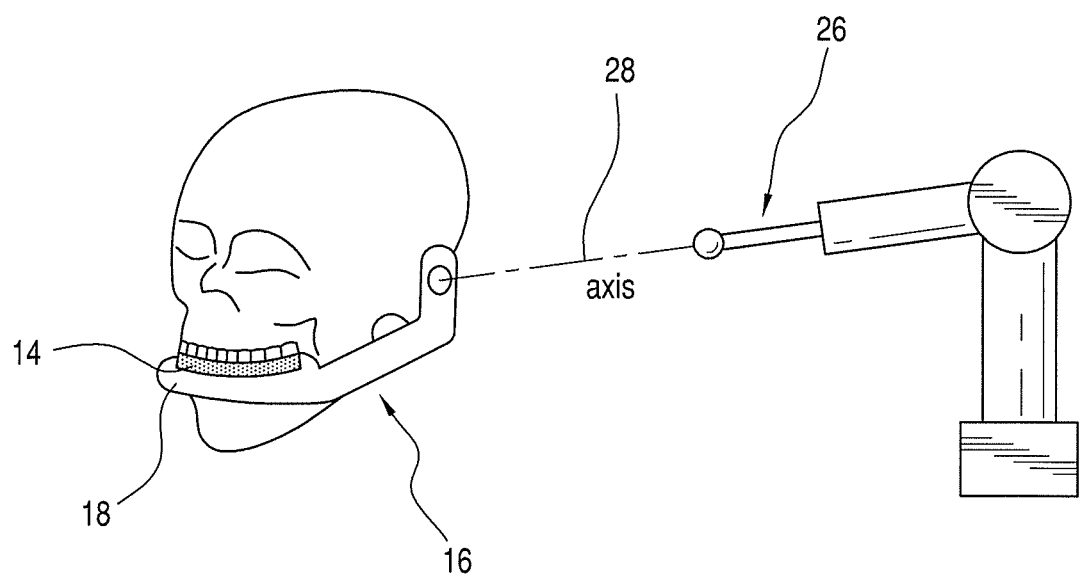
FIG. 6

CUSTOMIZED DRILLING JIG FOR IMPLANTATION OF A HEARING AID

BACKGROUND OF THE INVENTION

1. Field of the Invention

The present invention relates to a drilling jig for implantation of a hearing aid and to a method of producing such hearing aid. The invention also relates to a method of implanting a hearing aid by using such jig.

2. Description of Related Art

Typically, hearing aids are implanted without using automated drilling tools.

German Patent Application DE 100 49 938 A1 relates to a surgery method wherein, during surgery, a helmet-like instrument holder comprising a shell is fixed on the patient's head, with the shell of the instrument holder in addition being fixed at the teeth of the patient. The instrument holder is used for positioning a drilling jig in a defined manner. Prior to surgery, images of the respective part of the patient's body are taken.

German Patent DE 197 28 864 C2 relates to a method for dental surgery which uses a jig comprising openings for receiving titanium sleeves for guiding the drilling instrument for dental implantation. The jig is fixed at some of the teeth. An image of the patient's mouth is taken with the jig in place, wherein the sleeves act as markers. The position of the sleeves in the jig is modified according to the image prior to using the jig for surgery.

SUMMARY OF THE INVENTION

It is an object of the invention to provide for a tool which enables fast, easy, safe and inexpensive implantation of a hearing aid. It is also an object to provide for a method of producing such tool. It is a further object to provide for a corresponding method of implanting a hearing aid by using such tool.

According to the invention, these objects are achieved by a method of producing a drilling jig, a customized drilling jig and a method of implanting a hearing aid using such customized jig as described herein.

The invention is beneficial in that, by providing for a customized drilling jig comprising a print of the patient's upper teeth and a lateral beam with a drilling guide opening designed to guide the drilling tool along a minimally invasive drilling axis for drilling a cavity into the patient's head for implantation of the hearing aid, with the drilling axis having been previously determined based on a three-dimensional image of the patient's head produced prior to surgery with a standard jig positioned at the patient's head by using the teeth print, the drilling tool can be guided during surgery in a reliable manner along the previously determined minimally invasive drilling axis, whereby precision of the surgery can be improved and duration of the surgery can be reduced. In particular, the customized jig can be produced prior to surgery outside the operation room.

These and further objects, features and advantages of the present invention will become apparent from the following description when taken in connection with the accompanying drawings which, for purposes of illustration only, show several embodiments in accordance with the present invention.

BRIEF DESCRIPTION OF THE DRAWINGS

FIG. 5 is a perspective view of the patient's skull with a minimally invasive drilling axis, wherein the jig is shown prior to being provided with a drilling guide opening; and FIG. 6 is a perspective view of the patient's skull with the customized jig in place when used in surgery with a drilling tool.

DETAILED DESCRIPTION OF THE INVENTION

Figure 1:
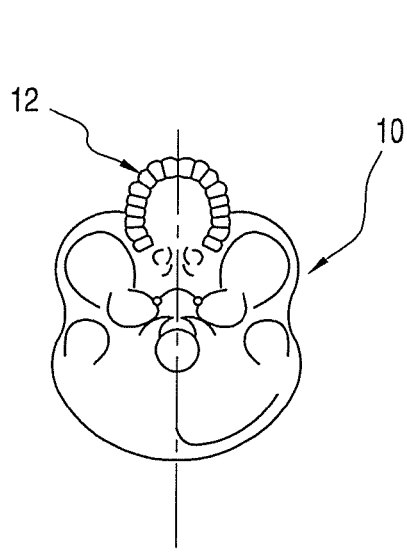
FIG. 1 is a view of a patient's skull without mandible seen from below.
Figure 2:
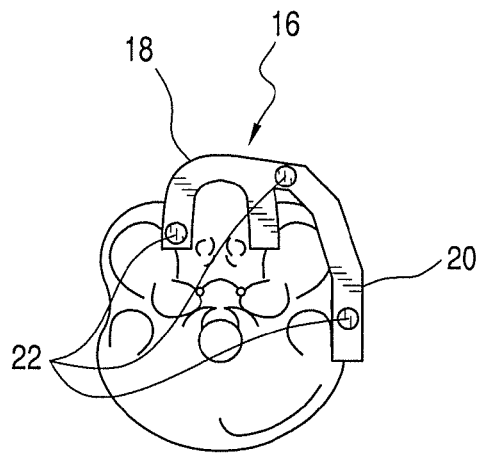
FIG. 2 is a view like FIG. 1, but with a customized drilling jig according to the invention having been put into place.

In order to produce a customized drilling jig for implantation of a hearing aid, first a print (molded imprint) 14 of the patient's upper teeth 12 is captured by solidifying an appropriate elastic material, in a manner as it is done by a dentist. Then, the molded imprint of the teeth 14 is connected to a jig 16 comprising a U-shaped portion 18 for connecting to the molded imprint 14 and a lateral beam 20 that is connected to the portion 18 is positioned extending up to the region behind patient's ear. The jig 16 is radiolucent and comprises at least three navigation benchmarks 22 which are radioopaque (see, FIG. 2).

A three-dimensional image of the patient's skull 10 with the jig 16 having been positioned at the patient's head 10 by using the molded imprint 14 is taken, for example, by using a computer tomography (CT) device.

Then, a navigation simulation procedure is carried-out on the base of the three-dimensional image of the patient's skull 10 and the position of the navigation benchmarks 22 on the image are used in order to determine a minimal-invasive drilling axis 28 for hearing aid implantation (see, FIG. 5). Such a simulation is performed out of the operation room. The position and orientation of a customized drilling guide opening 24, which is to be provided at the lateral beam 20 of the jig 16 for guiding a drilling tool 26, is determined from the determined minimal invasive drilling axis and the position of the jig 16 relative to the patient's head 10 (this relative position is determined by the molded imprint 14).

Figure 3:
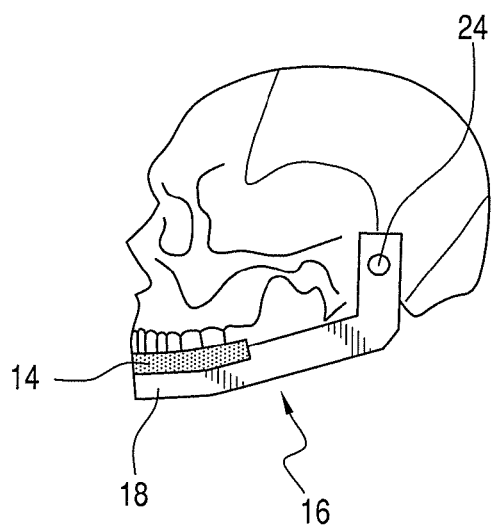
FIG. 3 is a side view of the patient's skull with the jig in place.
Figure 4:
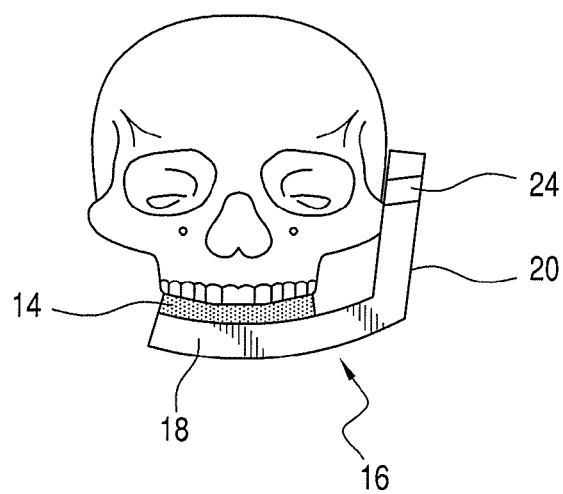
FIG. 4 is a front view of the patient's skull with the jig in place.

The thus obtained data and the jig 16 are sent to an external manufacturer (i.e., one outside of the operating room) who manufactures a customized jig 16, based on this data, with the customized drilling guide opening 24 in the lateral beam 20 of the jig 16 using an appropriate tool (the opening 24 is shown in FIGS. 3, 4 and 6).

Surgery then is performed by using the customized jig 16 (see, FIG. 6). To this end, first, the jig 16 is positioned on the patient's head 10 using the mold imprint 14 as a positioning element, the mandible acting as a type of natural clamp. Then, a cavity for implantation of the hearing aid is drilled into the patient's head using a drilling tool 26 which is guided by the drilling guide opening 24 of the jig 16. A navigation system or a CT device can be used to check the drilling progress. Prior to the operation, the position of the drilling tool 26 relative to the patient's head 10 may be checked using X-rays. The drilling depth and the creation of simply-shaped cavities (for example, step-shaped cavities) can be controlled by the navigation system or by using mechanical blocking means provided at the drilling guide opening 24 of the jig 16. In particular, such control is used to block the drilling tool 26 when a predetermined depth is reached.

In case of an emergency, the jig 16 can be removed from the teeth 12 in a very short time (a few seconds).

At the end of the procedure, the jig 16 can be discarded.

The actually obtained cavity may be compared with the determined minimal invasive drilling axis in order to statistically refine the procedure of determining the minimal invasive drilling axis.

The present invention allows for minimal-invasive implantation of hearing aids with a short surgical duration, whereby exposure and risk for the patient is minimized. No invasive navigation marks are necessary, and no special equipment, technical adjustment and engineers are needed in the operating room, so that the proposed procedure is suitable for any clinic doing auditory implants. The invention also allows for simpler and more robust hearing aid designs. Finally, the costs of the jig will be low.

The present invention can be used, for example, for implanting electro-mechanical hearing aid actuators, such as actuators for direct acoustic cochlear stimulation, and for implantation of cochlear electrodes. Typically, the hearing aid comprises a cylindrical housing to be inserted into the cavity.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method of producing a customized drilling jig for implantation of a hearing aid, comprising:
    capturing a dental imprint of a patient's upper teeth by solidifying an elastic material thereon;
    connecting a jig having a lateral beam and navigation benchmarks to the dental imprint;
    positioning the jig on the patient's head by using the dental imprint;
    capturing a three-dimensional image of the patient's head with the jig in place;
    determining a minimal invasive drilling axis for the hearing aid implantation based on the three-dimensional image; and
    manufacturing the customized drilling jig by providing the lateral beam of the jig with a drilling guide opening for guiding a drilling tool, wherein a position and orientation of the drilling guide opening are selected to guide the drilling tool along the determined minimal invasive drilling axis when the customized drilling jig is positioned at the patient's head using the dental imprint.

2. The method of claim 1, comprising, prior to manufacturing the customized drilling jig, sending the jig and data concerning the three-dimensional image and the determined drilling axis to a jig manufacturer, wherein the drilling guide opening is drilled into the lateral beam.

3. The method of claim 1, wherein the jig is radio-lucent.

4. The method of claim 3, wherein the benchmarks are radio-opaque.

5. The method of claim 1, wherein at least three benchmarks are provided.

6. A method of implanting a hearing aid using a customized drilling jig, comprising:
    capturing a dental imprint of a patient's upper teeth by solidifying an elastic material on the patient's upper teeth;
    connecting a jig having a lateral beam and navigation benchmarks to the dental imprint;
    positioning the jig on the patient's head held by the dental imprint against the patient's teeth;
    capturing a three-dimensional image of the patient's head and the benchmarks with the jig in place held by the dental imprint against the patient's teeth;
    determining a minimally invasive drilling axis for the hearing aid implantation based on the three-dimensional image captured;
    manufacturing the customized drilling jig by providing the lateral beam of the jig with a drilling guide opening for guiding a drilling tool, wherein a position and orientation of the drilling guide opening are selected so as to be able to guide the drilling tool along the determined minimally invasive drilling axis when the customized drilling jig is positioned on the patient's head held by the dental imprint against the patient's teeth;
    positioning the customized drilling jig held by the dental imprint against the patient's teeth;
    drilling a cavity for the implantation of the hearing aid into the patient's head using the drilling guide opening in the customized drilling jig for guiding the drilling tool; and
    implanting the hearing aid into the cavity.

7. The method of claim 6, wherein, for a plurality of cases, the actually obtained cavity is compared with the determined minimally invasive drilling axis in order to statistically refine the procedure of determining the minimally invasive drilling axis.

8. The method of claim 6, wherein a navigation system or a CT device is used for monitoring the drilling action.

9. The method of claim 6, wherein a drilling depth is controlled by a navigation system or by providing the customized drilling jig with mechanical means for blocking the drilling tool when a predetermined depth is reached.

10. The method of claim 6, wherein the hearing aid comprises a cylindrical housing to be inserted into the cavity.

* * * * *